United States Patent [19]

Hunt et al.

[11] Patent Number: 4,896,211

[45] Date of Patent: Jan. 23, 1990

[54] ASYNCHRONOUSLY TRIGGERED SINGLE FIELD TRANSFER VIDEO CAMERA

[75] Inventors: Robert P. Hunt, Palto Alto; Martin Shih, San Jose, both of Calif.

[73] Assignee: Picker International, Inc., Highland Heights, Ohio

[21] Appl. No.: 186,446

[22] Filed: Apr. 26, 1988

[51] Int. Cl.$^4$ .......................... H04N 3/14; H04N 7/18
[52] U.S. Cl. .................................... 358/106; 358/101; 358/213.26; 358/213.29
[58] Field of Search ................. 358/101, 106, 107, 93, 358/909, 213.13, 213.23, 213.25, 213.26, 213.29; 382/8; 356/237; 250/223 B, 562, 563, 572, 578

[56] References Cited

U.S. PATENT DOCUMENTS

| | | | |
|---|---|---|---|
| 4,737,846 | 4/1988 | Tokuno et al. | 358/101 X |
| 4,740,828 | 4/1989 | Kinoshita | 358/213.29 X |
| 4,794,453 | 12/1988 | Gnuechtel et al. | 358/101 |

OTHER PUBLICATIONS

"Frame Transfer Sensor" Philips Development Data, Feb. 1987, pp. 1–21.
"MS–4000 Series of High Resolution RS–170 and CCIR CCD Cameras", Product Data of Sierra Scientific, Oct. 1987.

Primary Examiner—James J. Groody
Assistant Examiner—Victor R. Kostak
Attorney, Agent, or Firm—Fay, Sharpe, Beall, Fagan, Minnich & McKee

[57] ABSTRACT

As an object moves along a conveyor (A), a position sensor (B) generates a trigger signal. The trigger signal causes a strobe (14) to emit a high intensity flash of light into an examination region. A lens (20) of a CCD camera (C) focuses light from the examination region both before and during the flash on an image section (24) of a CCD array (22). Subsequent to the flash, a trigger signal delay circuit (16) causes a control circuit (D) to shift the lines of pixel values from the image section into a storage section (26), from the storage section to shift registers (32), and serially from the shift register as a video signal. A video signal channel (52) refines the video signal which is transferred to a computer system (E) which implements a preselected quality control algorithm selected in accordance with a product to be examined. The control circuit includes a pulse generator (74), which provides the appropriate clocking pulses to transfer the data among the image section, the storage section, and the shift registers. A line counter (80) counts the lines of pixel values transferred from the image section. When the count corresponds to one field of a video image, the counter causes gates (96, 98) to stop passing clock pulses to the image and storage sections for transferring pixel values therebetween.

16 Claims, 3 Drawing Sheets

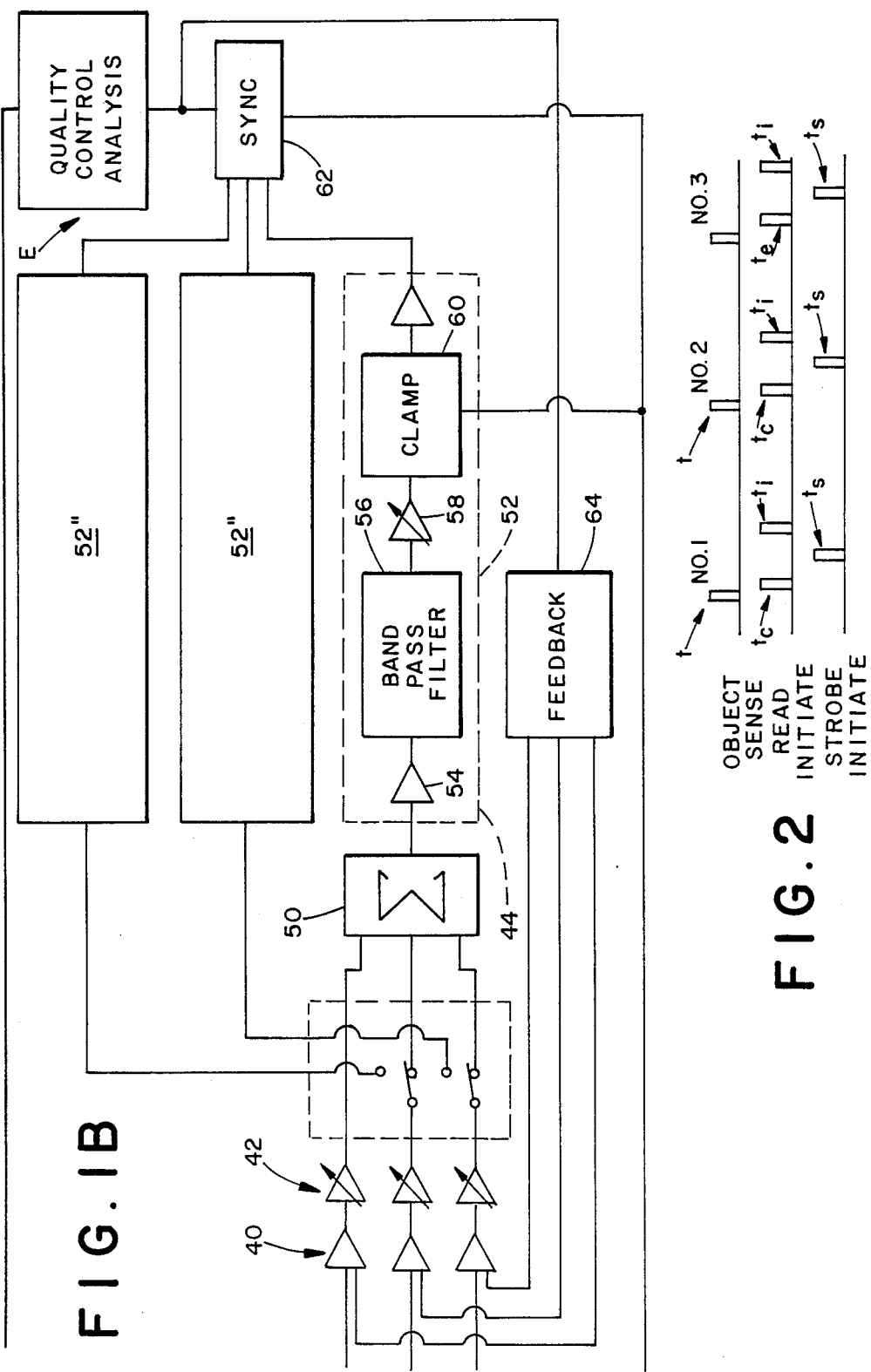

ASYNCHRONOUSLY TRIGGERED SINGLE FIELD TRANSFER VIDEO CAMERA

BACKGROUND OF THE INVENTION

The present invention relates to the video camera art. It finds particular application in conjunction with quality control and monitoring with video cameras and will be described with particular reference thereto. It is to be appreciated that the invention may find other applications including stop action photography, photographic archiving recording of slowly unfolding events, intermittent condition monitoring, video security, and the like.

Heretofore, charge coupled device (CCD) and other video cameras have generated a video output signal which included a long, continuous series of video image fields. In a transfer CCD camera, light was focused on an image section of a CCD sensor for a selected interval of time. The interval was selected to produce good image contrast with the amount of light received, e.g. 1/60th of a second. The charge on each element of the image section was indicative of received light intensity. The charge was transferred during a vertical blanking interval, e.g. a few hundred microseconds, into corresponding elements of an optically insensitive mass storage section. As the image section again commenced integrating received light, the charge was read out from the optically insensitive elements in the storage section element by element to form output values of a video signal representing one field of the resultant image. After the 1/60th of a second or other selected field interval, the charge representing the second field was transferred from the image section to the storage section. The image section started integrating light to form a third field and second field data was read from the storage section onto the video signal output. This sequence was repeated cyclically to form a video signal representing a series of single image fields.

This continuous production of image fields rendered CCD cameras awkward to adapt for certain high volume quality control situations. As objects were moved past the CCD camera, the resultant video signal represented a long series of image fields. In order to review the images of each object to monitor for a controlled characteristic, it was first necessary to determine which portion of the video signal included the field(s) which represented the monitored object. Second, it was necessary to determine within the field the actual location of the object. When increased lighting was necessary, the actuation of a strobe light was coordinated with the field of interest. If the strobe light was not completely coincident with a common location of the object within the field(s) of interest, lighting intensities and object shapes would vary among the fields of interest for each object. If the objects were moving rapidly compared with 1/60th of a second or other one field exposure time, then each object would be in a different position within the selected field of interest. This different positioning of the object not only required identifying the object position in the video field, but could also result in different lighting conditions on the object. These inaccuracies in the timing, positioning, and lighting of the monitored objects all limited the degree of accuracy and the speed with which quality control monitoring could be performed.

The present invention contemplates a new and improved video camera system which overcomes the above referenced problems and others.

SUMMARY OF THE INVENTION

In accordance with one aspect of the present invention, an asynchronously triggered CCD camera is provided. A lens focuses light from an examination region onto elements of an image section of a CCD light sensor array. A normally quiescent timing and control means responds to a trigger signal by causing a series of clock pulses for rapidly transferring optically induced charge or pixel values from elements of the image section into corresponding elements of a storage section. Additional clock pulses control transferring pixel values out from each element of the storage section to produce a single, serial video signal representing a single field of an image.

In accordance with a more limited aspect of the present invention, a quality control system is provided. A conveying means transports an object to be examined through an examination region. An object position sensor generates a trigger signal in response to the transportation of the object through the examination region. A first trigger signal causes a field of information to be clocked out, thereby "sweeping clean" the sensor of any charge build-up due to stray light or dark current. A second trigger signal causes a strobe of light followed by read out of the image. The strobe produces a flash of intense light in the examination region in response to the second trigger signal. Light from the examination region is focused on elements of a video camera CCD light sensor by a suitable lens or optical system. The light sensor includes an array of light sensitive elements which are each sensitive to light received through the lens to produce a pixel value that is indicative of the amount of light received. A transfer means is triggered by the first trigger signal from the object position sensor to flash the sensor and by the second trigger signal to transfer the pixel value from each element into a video signal representing a single field of a video image.

In accordance with a more limited aspect of the inventory, the first trigger signal initiates the flush cycle. A delay means delays the first trigger signal until the object arrives at a measured, reference position and uses the delayed first trigger signal to actuate the strobe. A control means controls the transfer means such that none of the element outputs are read until the delayed trigger pulse is received. In response to the delayed trigger pulse, each pixel value is read only once. In this manner, the generated video signal represents only a single video image field in which the object is at or near a preselected position in the examination region, hence, the image field.

In accordance with another aspect of the present invention, a method of monitoring with a video camera is provided. The video camera is focused on an examination region. An object is moved through the examination region under relatively subdued light. As the object moves through a predetermined position in the examination region, the object is illuminated with a high intensity light flash of a short duration. A light sensor of the video camera integrates both the subdued light and the high intensity light received from the examination region as the object is transported therethrough. Subsequent to the high intensity flash, integrated light values are read from the light sensor to produce a video signal which represents a single field of a video image.

In accordance with a more limited aspect of the method, the single field image representation of the video signal is analyzed to determine at least one characteristic of the object. The method may be repeated to sort a plurality of objects in accordance with the determined characteristic. If the object is a continuous web, the camera takes single field images of contiguous web segments and records the spatial location of any noted surface blemishes, pattern defects, discontinuities, and the like.

A first advantage of the present invention is that a video camera is asynchronously triggered to scan an image at a controlled instant in time to "grab" a moving object.

Another advantage of the present invention is that it provides a variable optical image time integration.

Yet another advantage of the present invention is that it facilitates digital image processing for pattern recognition on moving objects.

Still further advantages of the present invention will become apparent to those of ordinary skill in the art upon reading and understanding the following detailed description.

BRIEF DESCRIPTION OF THE DRAWINGS

The present invention may take form in various components and arrangements of components or in various steps and arrangements of steps. The figures are only for purposes of illustrating a preferred embodiment and are not to be construed as limiting the invention.

FIG. 1A and 1B provide is a diagrammatic illustration of a quality control system in accordance with the present invention;

FIG. 2 is a timing diagram for the system of FIG. 1; and,

DETAILED DESCRIPTION OF THE PREFERRED EMBODIMENT

Figure 1A:
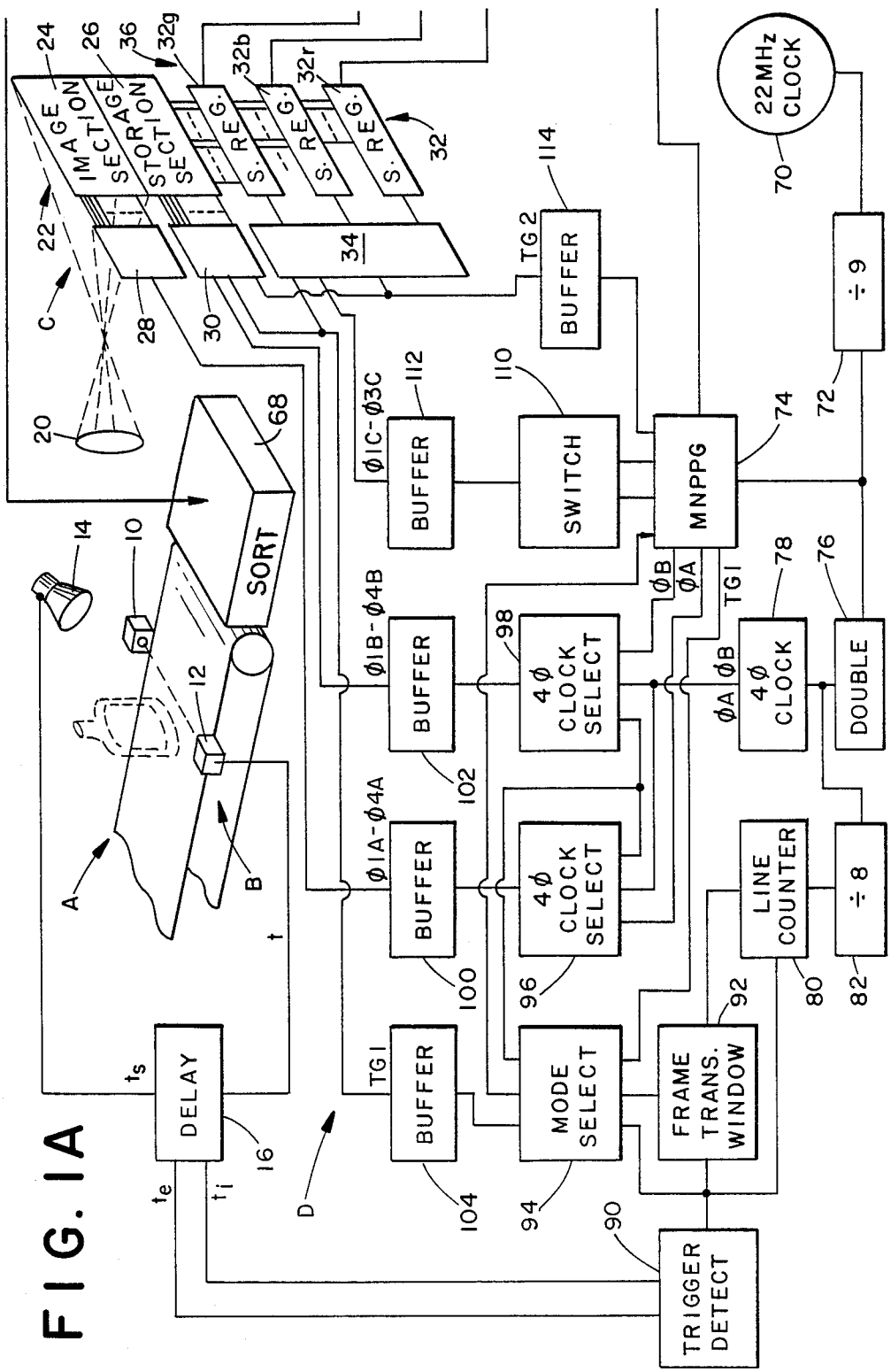

With reference to FIG. 1A and 1B, a conveying means A transports articles to be examined through an examination region. A position sensor B senses transportation of an object to a preselected position within the examination region. A CCD video camera C with video processing circuitry that provides precision digitization and digital signal processing of the resultant video signal generates a video signal which represents a single field of an image of the object. A clock or reading means controller D is triggered by the object position sensing means B each time an object passes to enable the camera to collect the single field image. A signal processing means E operates on each single field video signal to determine one or more selected characteristics of the object.

In the embodiment of FIG. 1A and 1B, the conveying means A includes a conventional conveyor for moving objects O through the examination region. The nature of the conveyor will vary with the object to be transported, as is known in the art. For example, the conveyor may include a belt for carrying the articles. Optionally, the conveyor may have pockets, recesses, or clamps for fixing the position of each received object on the belt. As a more specific example, the conveyor might have pockets to convey transparent bottles that are filled with a liquid and have a rectangular label on one face thereof. Other conveying systems such as pneumatic, magnetic, gravity, and the like are also contemplated.

The object position sensing means B in the exemplary, illustrated embodiment include a light source 10 and photocell 12 which generates a trigger signal t in response to the object O breaking the beam, i.e. coming into the examination region. Other position detectors are also contemplated such as a mechanical finger, a capacitive proximity detector, a gear arrangement driven by the conveyor, a reed switch, and the like. The trigger signal is conveyed to a strobe lamp 14 by way of a delay means 16 to cause a short duration high intensity flash in the examination region.

The camera C includes an optical system such as a lens 20 which focuses light received from the examination region on a light sensing means 22, such as a bidirectional array of CCD elements. Conventionally, a CCD camera includes an image section 24 which receives light from the lens and an optically insensitive storage section 26 which is masked from light. The lens focuses light emanating from the examination region continuously onto the image section. The relative intensity and duration of the subdued light between strobe flashes and the high intensity light during the strobe flash are selected such that the vast majority of the light received by the image section originates during the strobe flash. Preferably, the subdued light from between strobe flashes accounts for less than 5% of the total light received and the strobe flash accounts for 95% or more. The resolution of the resultant image is determined by the number of CCD elements in each dimension. The more elements, the finer the resolution. A typical video camera might have a 244×610 element array. For color, three times as many elements are provided. A third of the elements have a green filter, a third a blue filter, and a third a red filter or other three color filter combination as is conventional in the art.

The data is shifted from the image section to the storage section during the vertical fly back period which erases or resets each element of the image section. Because only subdued light is received during the fly back period and because the fly back period lasts only about a millisecond, the continued exposure to subdued light from the examination region has a minimal effect on the total light received.

With reference to FIG. 2, the trigger signal t is conveyed to the delay means 16. The delay means conveys a light sensor cleaning or sweep trigger signal $t_c$ to the controller D to cause any accumulated charge on the image sensor 24 to be transferred and discarded or otherwise removed. A strobe trigger signal $t_s$ is conveyed to the strobe 16 to cause the high intensity flash. The strobe signal follows the clean trigger signal $t_c$ by a duration commensurate with the time required to sweep the accumulated charge from the light sensor. An image trigger signal $t_i$ is conveyed to the controller D immediately following the strobe flash to cause charge accumulated during the strobe flash to be transferred and become the resultant image.

When the controller D receives the image trigger signal $t_i$, it conveys clock pulses to an image transfer clock or means, including an image section control means 28 and a storage section control means 30. The image transfer means causes the charge of each image element of the image section to be shifted to a corresponding element in the storage section. More specifically, each image transfer clock pulse shifts the charge one line. After just about 250 pulses in the illustrated 244 active line image section embodiment, the charges have been shifted 244 lines fully into the storage section 26. The clocking signals are selected such that the image transfer requires only a few milliseconds and occurs while subdued light is being received. After the charge level information is transferred to the storage section, the controller D stops the image transfer clock pulses. The controller conveys lower speed storage transfer clock pulses to the storage section control means 30 to cause the data from the storage section to be shifted line by line into a shift register means 32.

For a color video image rendition, a red shift register 32r, a blue shift register 32b, and a green shift register 32g are provided. Once a line of data has been transferred from the storage section 26 to the shift registers, the controller D sends higher speed shift register clock signals to a shift register controller 34. The shift registers serially step each charge or data value onto output lines 36 before the next line is loaded into the shift registers from the storage section. Thus, between storage transfer clock pulses, a number of shift register clock pulses equal to the number of elements per line are generated.

Feedback amplifiers 40 combine each of the three color output signals with a feedback signal which establishes a DC reference level to minimize the interfering effects of clock noise. A gain adjusting amplifier means 42 adjusts the gain of all three signal components correspondingly. A black and white/color mode selecting means 44 selects whether a black and white or color composite video signal is to be produced.

If a black and white image is selected, a summing means 50 sums the three color components corresponding to each pixel and feeds the data to a first video signal processing channel 52. The video channel includes an impedance adjusting amplifier 54 for providing a low impedance output signal. A band pass filter 56 removes any vestiges of clocking signal noise or the like. A user controlled gain amplifier 58 amplifies the signal from the band pass filter and passes it to a clamping means 60 which restores the DC video. Conventionally, at the end of each horizontal sweep line, the clamping means shorts to a DC reference level to restore a DC level that sets the black level of the resultant image. A synchronization information means 62 switches between lines and fields to reference voltages to add blanking and vertical and horizontal synchronization information to the signal as is conventional. A feedback circuit 64 feeds back a portion of the composite video signal to provide a phase sensitive detection of the clocking to establish the DC level that minimizes the clock noise.

If a color output is selected, then the switching means 44 connects two components of the output signal to analogous video processing channels 52', 52". By convention, the synchronization means 52 only adds synchronization information to one, generally the green, video component. Preferably, the feedback signal also is based on a single one of the components. The video processing circuitry is stable to better than one part in 256 to enable precision digitizing and digital signal processing of the resultant video signal.

The quality control analysis means E receives the composite video signal and operates on it in a manner that is appropriate to the quality control function undertaken. For example, the analysis means E may turn the composite signal into a man-readable video image. Alternately, the analysis means may examine components of the video signal corresponding to selected regions to determine whether they meet preselected characteristics. Looking to the above referenced example in which the objects are transparent bottles filled with liquid and carrying a label, each bottle is defined by a change in gray scale relative to the rest of the image region. The periphery of the bottle is compared with a preselected periphery to determine if the bottle is broken or deformed beyond selected tolerances. The fill level of the liquid in the bottle is similarly denoted by a change in gray scale along a horizontal interface. The level or height of the horizontal interface is compared with a standard to determine whether the bottle is fully filled. Analogously, the label is denoted by a change in gray scale relative to the liquid filled bottle. The position of the label region is compared with preselected label placement tolerances to see if the label is appropriately positioned. The top label interface is compared with horizontal to determine if the label is straight. The distance between the top and bottom and the left and right edges of the label are measured to determine whether the label is folded or creased. If the objects are monitored in color, a colorimetric examination of the contents of the bottle, the printing on the label, or the like may also be performed. Further, color or other physical parameters may be used to sort various types of acceptable products. A sorting means 68 may be operated under the control of the quality control analysis means E for sorting objects in accordance with such determined characteristics or parameters. Numerous other sorting, quality control, and acceptance algorithms may be implemented as are appropriate to the requirements of the objects being examined.

The controller D includes a 22 MHz or other clock means 70 which continuously provides clock or timing pulses. A frequency divider 72 divides the frequency by 9 in the specific example to produce a 2.5 MHz control clock signal. A multi-norm pulse pattern generator (MNPPG) 74 converts the 2.5 MHz clock signal to the above discussed control clock signals for the image transfer control means 28, the storage transfer control means 30, and the shift register control means 34. More specifically, it provides four phases $\phi 1A-\phi 4A$ of the field transfer clock for the image section and four phases $\phi 1B-\phi 4B$ of the field transfer clock for the storage section. Three control clock phases $\phi 1C-\phi 3C$ are provided for controlling transfer of data from the shift registers 32. It also provides two transfer gate pulses TG1 and TG2, optical blanking and clamping pulses for the clamping means 60 and the sync means 62, and start and stop pulses.

A doubler 76 doubles the main clock frequency to 5 MHz. A four phase clock signal generator or shift register 78 produces vertical clamping pulses for controlling the image and storage transfer clocks. A field transfer line counter 80 counts the number of lines transferred from the image section to the storage section, 251 lines in the preferred embodiment. A frequency adjusting means 82 adjusts the frequency of the clock pulse to match the rate at which lines are transferred, i.e. divides the doubled frequency by eight in the preferred embodiment.

A trigger detecting means 90 receives the cleaning and image trigger signals $t_c$, $t_i$ from the delay circuit 16. In response to the image trigger signal, the trigger detecting means 90 sets a field transfer window pulse latch or flip-flop 92 and resets the line counter 80. The field transfer window pulse latch produces an enable signal for the length of one field transfer—251 lines in the preferred embodiment. The field window or enable signal is conveyed to a mode selector switch means 94 which selects whether the camera is operating in the trigger mode of the present invention or in a normal camera mode. In the trigger mode, the trigger pulse, the field transfer window signal, and the transfer gate storage signal TG1 are conveyed through the mode selection switch. The field conveyed to first and second four phase clock selector means 96 and 98 which select either the four phase clock signal from the multi-normal pulse pattern generator 74 or the clock signal from the four phase clock generator 78. The selected clock signals $\phi A$ and $\phi B$ from either the multi-normal pulse pattern generator 74 or the four phase clock generator 78 are gated through to buffers 100, 102 and to the image and storage transfer control means 28 and 30. A buffer 104 conveys the transfer gate storage signal TG1 to the output register control means 34. The trigger pulse is conveyed through as a reset signal to the multi-normal pulse pattern generator 74.

The three phase control clock $\phi C$ from the multi-normal pulse pattern generator 74 are conveyed to a switch means 110 which is controlled by the start and stop signal. Between the start and stop signals, the switch means 110 conveys the control clock signals through a buffer 112 to the shift register control means 30. Another buffer 114 conveys the second transfer gate signal TG2 to the shift register control means.

Briefly summarized, the clock means produces output signals $\phi 1A-\phi 4A$ and $\phi 1B-\phi AB$ for shifting data from the light sensitive region to the storage region and clock signals TG1 and TG2 for shifting data from the storage region into the shift registers 32. The clock means further provides shift register clock signals $\phi 1C-\phi 3C$ for shifting the data out of the three shift registers to form lines of the video signal. The mode selector means 94 causes the clock selecting means 96, 98 to pass either the continuous clock signals from the clock means 76, 78 or the intermittent, selectively triggered clock signals from the multi-normal pulse pattern generator 74. In the asynchronously triggered mode, the multi-normal pulse pattern generator signals are passed to vertical line drivers 28, 30 for the image and storage sections, respectively. The vertical line counter 80 counts the number of lines of data transferred. Once an entire field is passed, 251 lines in the preferred embodiment, the vertical line counter signals the mode selector 94 which disables the clock selector means 96, 98 such that the transfer of data is stopped. The mode selection means further resets the multi-normal pulse pattern generator means 74 in response to each trigger signal such that the shift register control signals are synchronized with the clock signals.

Figure 3:
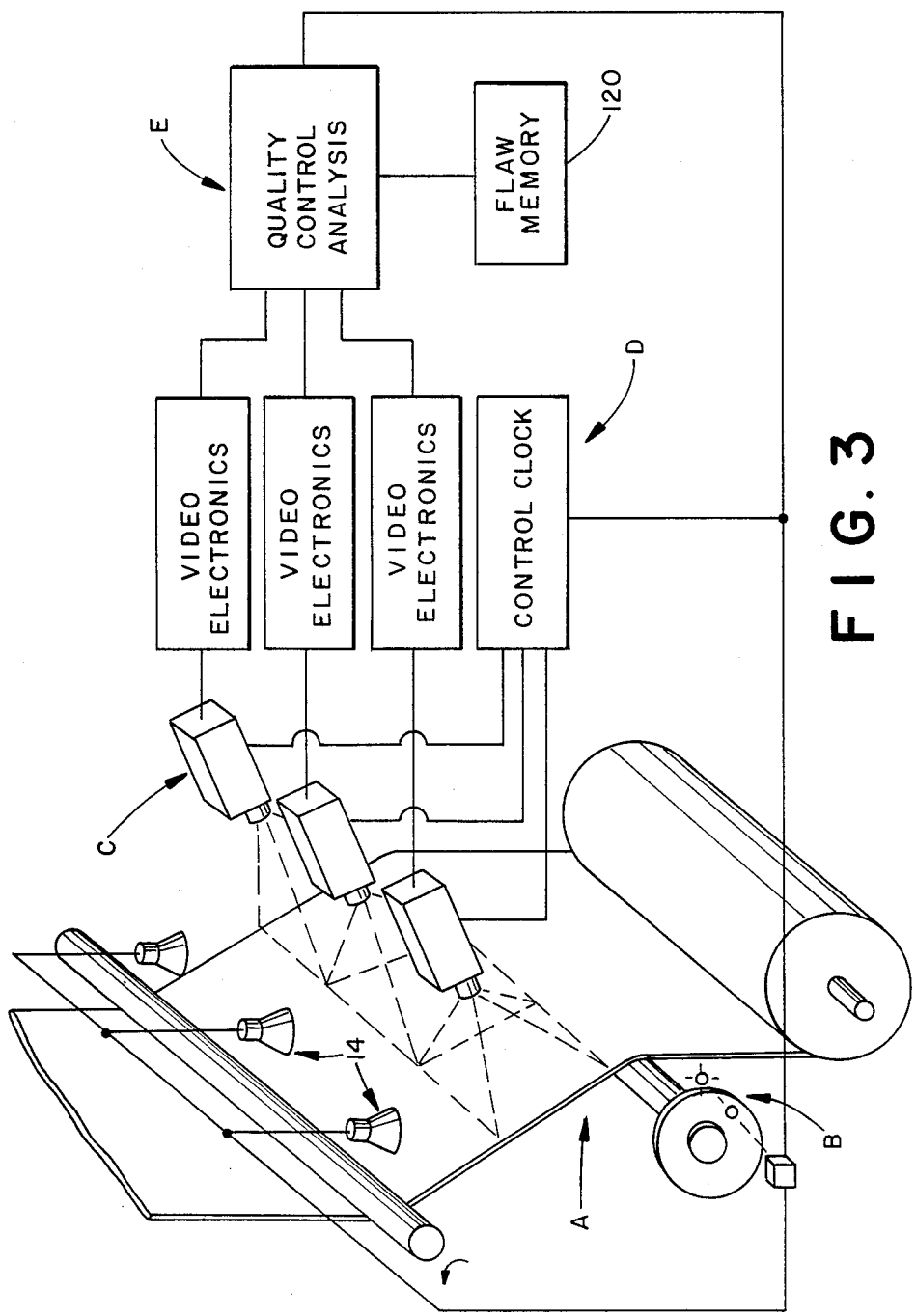
FIG. 3 is a diagrammatic illustration of an alternate embodiment of the quality control system for monitoring continuous webs.

With reference to FIG. 3, an alternate embodiment of the present invention is provided. The examined object is a continuous web and the conveying means A includes rollers or feed guides for feeding the web through the examination region. The position sensor B includes a gearing arrangement, such as a light/photocell assembly which periodically shines through an aperture attached to the guide rollers, to designate that an incremental length of the continuous web product has passed through the examination region. In the preferred embodiment, the position sensor creates a trigger signal each time a length of the web commensurate with the length of the examination region passes, e.g. each foot. The control clock means D provides the same clock signals concurrently to each of the cameras.

Preferably, the size of the examination region is commensurate with the repeat of a pattern on the web. In this manner, a square foot of the web product is viewed by the camera C and analyzed by the analyzing means E. The analyzing means compares the pattern of the sheet goods with a preselected pattern, looks for surface flaws such as pits, bubbles, color or gloss discontinuities, and the like. The position of each flaw is recorded on a man readable print-out or display or in a flaw memory 120. That is, the distance from the end of the roll is recorded as one coordinate. The other position coordinate or distance from an edge is determined from the camera which produced the image of the flaw and the flaw position within the field. Where appropriate, the nature of the flaw can also be recorded. To examine the full width of the web product, additional cameras are provided. To examine a three foot web, three or more cameras may be provided depending on detail required. A plurality of strobes 14 is provided and each camera and strobe is synchronized such that all three regions across the web are imaged and analyzed concurrently.

The invention has been described with reference to the preferred embodiment. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiment, the invention is now claimed to be:

1. A method of quality control comprising:
  (a) focusing a video camera on an examination region;
  (b) moving an object to be examined through the examination region under relatively subdued light;
  (c) flushing accumulated charge from a light sensor of the video camera;
  (d) as the object moves through the examination region, illuminating the object with high intensity light from a high intensity flash;
  (e) on the light sensor, integrating both the subdued light and the high intensity light from the examination region;
  (f) subsequent to the high intensity flash, reading integrated light values from the light sensor to produce a video signal representing a single field of a video image;
  (g) determining at least one characteristic of the object from the single field video signal.

2. The method as set forth in claim 1 further including repeating steps (b) through (g) for each of a plurality of objects and sorting the objects in accordance with the determined characteristic.

3. The method as set forth in claim 1 wherein the object is a continuous web and further including repeating steps (b) through (g) at regular intervals and recording a spatial location of determined characteristics along the web.

4. The method as set forth in claim 1 wherein the light sensor is a CCD array and wherein the step of reading integrated light values from the light sensor includes:
  transferring pixel values from a light sensing image section rapidly to a storage section, resetting the image section and continuing to integrate subdued light from the examination region on the image section;

retrieving the pixel values from the storage region and forming them into the single field video signal.

5. The method as set forth in claim 4 further including adding blanking and synchronization information to the video signal.

6. A method of asynchronously triggering single field video signals, the method comprising:
   (a) receiving light on an image section of a CCD array;
   (b) in response to receiving a trigger signal, transferring lines of pixel values from the image section of the CCD array to a storage section;
   (c) transferring pixel values from the storage section serially onto an output line to create a video signal;
   (d) counting a number of lines of pixel values transferred from the image section to the storage section;
   (e) in response to counting a number of lines corresponding to a single field of a video image, terminating the transfer of lines of pixel values from the image section to the storage section;
   (f) in response to another trigger signal, repeating steps (b) to (e) to create another single field video signal.

7. A quality control system comprising:
   a conveying means for transporting an object to be examined through an examination region;
   an object position sensor means for generating a trigger signal in response to transportation of the object through the examination region;
   a strobe means for causing a flash of intense light in the image region in response to the trigger signal;
   an optical system for focusing light from the examination region onto a video camera light sensor;
   the light sensor including an image section having an array of light sensitive elements which are each sensitive to light received through the optical system to produce individual pixel values that are indicative of an amount of light received;
   a transfer means for serially transferring the pixel values from the light sensor to create a video signal representing an image of the examination region;
   a delay means for receiving the trigger signal and generating (i) a clean trigger signal for zeroing the pixel values of the light sensor, (ii) a strobe trigger signal for actuating the strobe means when the object is in a preselected position, and (iii) an image trigger signal for causing the transfer means to transfer the single video image field of pixel values;
   a control means for controlling the transfer means such that the pixel values are transferred in response to the trigger pulse only once whereby the video signal represents a single video image field.

8. The system as set forth in claim 7 further including at least one shift register, the transfer means transferring lines of pixel values from the storage section and transferring pixel values of each line as the video signal.

9. An inspection system comprising:
   a conveying means for transporting an object to be examined through an examination region;
   an object position sensor means for generating a trigger signal in response to transportation of the object through the examination region;
   a strobe means for causing a flash of intense light in the image region in response to the trigger signal;
   an optical system for focusing light from the examination region onto a video camera light sensor;
   the light sensor including:
   an image section having an array of light sensitive elements which are each sensitive to light received through the optical system to produce individual pixel values that are indicative of an amount of light received; a storage section;
   a transfer means for serially transferring the pixel values from the light sensor to the storage section and from the storage section to create a video signal representing an image of the examination region;
   a control means for causing the transfer means to transfer pixel values rapidly from the image section to the storage section in response to the trigger signal and serially to transfer the pixel values from the storage section to create the video signal while the image section receives light to produce pixel values for another field, the pixel values being transferred inn response to the trigger pulse such that the video signal represents a single video image.

10. The system as set forth in claim 9 wherein the control means includes a clock generator for generating clock pulses for controlling transfer of pixel values from the image section to the storage section, clock pulses for controlling transfer of pixel values from the storage section to the shift register, and clock pulse for controlling transfer of pixel values from the shift register;
   clock pulse gating means for selectively passing the clock pulses to the light sensor;
   a line counting means for counting a number of lines of pixel values transferred, the line counting means being operatively connected with the gating means for terminating the passing of clock pulses to the light sensor in response to the line count reaching a preselected line count indicative of one video image field.

11. A system comprising:
   a conveying means for transporting an object to be examined through an examination region;
   an optical system for focusing light from the examination region onto a video camera light sensor, the light sensor including an image section having an array of light sensitive elements which are each sensitive to light received through the optical system to produce individual pixel values that are indicative of an amount of light received;
   a transfer means for serially transferring the pixel values from the light sensor to create a video signal representing an image of the examination region;
   an object position sensor means for generating a trigger signal in response to transportation of the object through the examination region;
   a delay means for receiving the trigger signal and generating a clean trigger signal for zeroing the pixel values of the light sensor;
   a control means for controlling the transfer means such that the pixel values are transferred in response to the trigger pulse only once whereby the video signal represents a single video image.

12. An inspection system comprising:
   a conveying means for transporting an object to be examined through an examination region;
   an object position sensor means for generating a trigger signal in response to transportation of the object through the examination region;
   a strobe means for causing a flash of intense light in the image region in response to the trigger signal;

a delay means for receiving the trigger signal and generating a strobe trigger signal for actuating the strobe means when the object is in a preselected position;

an optical system for focusing light from the examination region onto a video camera light sensor;

the light sensor including an image section having an array of light sensitive elements which are each sensitive to light received through the optical system to produce individual pixel values that are indicative of an amount of light received;

a transfer means for serially transferring the pixel values from the light sensor to create a video signal representing an image of the examination region;

a control means for controlling the transfer means such that the pixel values are transferred in response to the trigger pulse only once whereby the video signal represents a single video image field.

13. An inspection system comprising:

an object position sensor means for generating a trigger signal in response to transportation of the object through an examination region;

an optical system for focusing light from the examination region onto a video camera light sensor;

the light sensor including an image section having an array of light sensitive elements which are each sensitive to light received through the optical system to produce individual pixel values that are indicative of an amount of light received;

a transfer means for serially transferring the pixel values from the light sensor to create a video signal representing an image of the examination region;

a delay means for receiving the trigger signal and generating an image trigger for causing the transfer means to transfer the single video image field of pixel values.

14. An asynchronously triggered single field video camera system comprising:

a CCD array including:

an image section having an array of light sensitive elements for accumulating pixel values indicative of a cumulative amount of light received;

a storage section having an array of pixel storage elements, the storage section being electrically connected with the image section such that the pixel values indicative of cumulative light received by each pixel is transferable from the image section to the storage section;

a shift register means for serializing the pixel values from the storage section into a video signal;

a shutterless lens for continuously focusing light on the image section;

a clock means for generating clock signals for (1) transferring pixel values from the image section to the storage section, (2) from the storage section to the shift register means, and (3) from the shift register means;

a gating means for selectively passing the clock signals from the clock means to the image section in response to an asynchronously received trigger signal;

a means for determining when a single video field of pixel values being transferred from the image section to the storage section;

a means for stopping the gate from passing clock signals to the image section in response to the determining means determining that a single video field has been transferred from the image section, whereby a single field of pixel values is passed from the image section to the storage section.

15. An asynchronously triggered single field video camera system comprising:

a CCD array including: 'an image section having an array of light sensitive elements for accumulating pixel values indicative of a cumulative amount of light received;

a storage section having an array of pixel storage elements, the storage section being electrically connected with the image section such that the pixel values indicative of cumulative light received by each pixel is transferable from the image section to the storage section;

a shift register means for serializing the pixel values from the storage section into a video signal;

a lens for continuously focusing light on the image section;

a clock means for generating clock signals for (1) transferring pixel values from the image section to the storage section, (2) from the storage section to the shift register means, and (3) from the shift register means;

a gating means for selectively passing the clock signals from the clock means to the image section in response to an asynchronously received trigger signal;

a counter means for counting clock signals;

a control means for causing the gate means to convey the clock signals to the image section in response to an asynchronously received trigger signal and for stopping the passing of clock signals for transferring values from the image to the storage section in response to the counting means reaching a count that indicates a single video field of pixel values has been transferred to the storage section;

a video processing circuitry means which is stable to better than one part in 256 to enable precision digitization and digital signal processing of the resultant video signal.

16. An asynchronously triggered single field video camera system comprising:

a CCD array including:

an image section having an array of light sensitive elements for accumulating pixel values indicative of a cumulative amount of light received;

an optically insensitive storage section having an array of pixel storage elements, the storage section being electrically connected with the image section such that the pixel values indicative of cumulative light received by each pixel is transferable from the image section to the storage section;

a shift register means for serializing the pixel values from the storage section into a video signal;

a shutterless lens for continuously focusing light on the image section;

a clock means for generating clock signals for (1) transferring pixel values from the image section to the storage section, (2) from the storage section to the shift register means, and (3) from the shift register means;

a control means for selectively controlling passing of clock signals to at least the image section such that the camera system operates selectively in one of an asynchronously triggered mode and a standard video camera mode; and a mode selection means for selectively enabling the control means to operate in one of the asynchronously triggered and standard modes.

* * * * *